United States Patent [19]
Gregg et al.

[11] Patent Number: 5,320,725
[45] Date of Patent: * Jun. 14, 1994

[54] ELECTRODE AND METHOD FOR THE DETECTION OF HYDROGEN PEROXIDE

[75] Inventors: Brian A. Gregg; Adam Heller, both of Austin, Tex.

[73] Assignee: E. Heller & Company, Austin, Tex.

[ * ] Notice: The portion of the term of this patent subsequent to Nov. 16, 2010 has been disclaimed.

[21] Appl. No.: 880,759

[22] Filed: May 8, 1992

Related U.S. Application Data

[63] Continuation-in-part of Ser. No. 389,226, Aug. 2, 1989, Pat. No. 5,262,035.

[51] Int. Cl.$^5$ .......................................... G01N 37/327
[52] U.S. Cl. ............................ 204/153.12; 204/403; 204/416; 204/418; 435/28; 435/817; 436/528; 436/531; 436/533; 436/535; 436/806
[58] Field of Search ............... 204/153.12, 403, 415, 204/416, 418; 435/28, 817; 436/528, 531, 533, 535, 806

[56] References Cited

U.S. PATENT DOCUMENTS

| | | | |
|---|---|---|---|
| 4,098,574 | 7/1978 | Dappen | 435/14 |
| 4,168,205 | 9/1979 | Danninger et al. | 435/25 |
| 4,224,125 | 9/1980 | Nakamura et al. | 435/817 |
| 4,247,297 | 1/1981 | Berti et al. | 435/24 |
| 4,356,074 | 10/1982 | Johnson | 435/190 |
| 4,375,399 | 3/1983 | Havas et al. | 435/14 |
| 4,390,621 | 6/1983 | Bauer | 435/14 |
| 4,404,066 | 9/1983 | Johnson | 435/817 |
| 4,418,148 | 11/1983 | Oberhardt | 435/14 |
| 4,427,770 | 1/1984 | Chen et al. | 435/14 |
| 4,461,691 | 7/1984 | Frank | 204/290 R |
| 4,476,003 | 10/1984 | Frank et al. | 204/290 R |
| 4,524,114 | 6/1985 | Samuels et al. | 204/290 R |
| 4,545,382 | 10/1985 | Higgins et al. | 204/403 |
| 4,552,840 | 11/1985 | Riffer | 435/28 |
| 4,619,754 | 10/1986 | Niki et al. | 204/403 |
| 4,655,885 | 4/1987 | Hill et al. | 204/294 |
| 4,711,245 | 12/1987 | Higgins et al. | 204/403 |
| 4,717,673 | 1/1988 | Wrighton et al. | 436/806 |
| 4,721,601 | 1/1988 | Wrighton et al. | 204/435 |
| 4,758,323 | 7/1988 | Davis et al. | 435/26 |
| 4,764,416 | 9/1988 | Ueyama et al. | 428/212 |
| 4,776,944 | 10/1988 | Janata et al. | 435/817 |
| 4,784,736 | 11/1988 | Lonsdale et al. | 540/122 |
| 4,795,707 | 1/1989 | Niiyama et al. | 435/817 |
| 4,917,800 | 4/1990 | Lonsdale et al. | 210/490 |
| 4,927,516 | 5/1990 | Yamaguchi et al. | 435/817 |
| 4,938,860 | 7/1990 | Wogoman | 435/817 |
| 4,968,400 | 11/1990 | Shimomura et al. | 204/403 |
| 5,082,786 | 1/1992 | Nakamoto | 435/14 |

FOREIGN PATENT DOCUMENTS

| | | |
|---|---|---|
| 127958A2 | 5/1984 | European Pat. Off. . |
| 0125139 | 11/1984 | European Pat. Off. . |
| 0184909 | 6/1986 | European Pat. Off. . |
| 0241309A3 | 4/1987 | European Pat. Off. . |
| 0278647 | 8/1988 | European Pat. Off. . |
| 0368209A1 | 6/1989 | European Pat. Off. . |
| 0390390A1 | 3/1990 | European Pat. Off. . |
| 55-012437A | 1/1980 | Japan . |
| 58-49821 | 11/1983 | Japan . |
| 58-049821B | 11/1983 | Japan . |
| 63-309848A | 12/1988 | Japan . |
| 2006737A | 1/1990 | Japan . |
| 2088960A | 3/1990 | Japan . |
| 2099850A | 4/1990 | Japan . |
| 830229A | 5/1981 | U.S.S.R. . |
| 1016306A | 5/1983 | U.S.S.R. . |

OTHER PUBLICATIONS

Foulds et al., "Immobilization of Glucose Oxidase in Ferrocene-Modified Pyrrole Polymers," *Anal. Chem.*, vol. 60, No. 22, pp. 2473-2478 (1988).

(List continued on next page.)

*Primary Examiner*—T. Tung
*Attorney, Agent, or Firm*—Pravel, Hewitt, Kimball & Krieger

[57] ABSTRACT

An amperometric biosensor and method for the detection of hydrogen peroxide, NADH, or NADPH with high sensitivity includes an electrode having on its testing surface a three-dimensional redox polymer network in which peroxidase is immobilized.

17 Claims, 9 Drawing Sheets

OTHER PUBLICATIONS

Hale et al., "A New Class of Amperometric Biosensor Incorporating a Polymeric Electron-Transfer Mediator", *J. Am. Chem. Soc.*, vol. 111, No. 9, pp. 3482-3484 (1989).

Foulds et al., "Enzyme Entrapment in Electrically Conducting Polymers", *J. Chem. Soc.*, Faraday Trans. 1, vol. 82, pp. 1259-1264 (1986).

Dengani et al., "Electrical Communication between Redox Centers of Glucose Oxidase and Electrodes via Electrostatically and Convalently Bound Redox Polymers", *J. Am. Chem. Soc.*, vol. 111, pp. 2357-2358 (1989).

Bartlett et al., "Strategies for the Development of Amperometric Enzyme Electrodes", *Biosensors*, vol. 3, pp. 359-379 (1987/88).

Clark et al., "Electrode Systems for Continuous Monitoring in Cardiovascular Surgery", *Ann. N.Y. Acad. Sci.*, vol. 102, pp. 29 (1962).

Clark et al., "Long-term Stability of Electroenzymatic Glucose Sensors Implanted in Mice", *Trans. Am. Soc. Artif. Inten. Organs*, vol. 34, pp. 259-265 (1988).

Cass et al., "Ferricinium Ion as an Electron Acceptor for Oxido-Reductases", *J. Electroanal. Chem.*, vol 190, pp. 117-127 (1985).

Albery et al., "Amperometric enzyme electrodes", *Phil. Trans. R. Soc. Long.*, vol. B 316, pp. 107-109 (1987).

Scheller et al., "Enzyme Electrodes and their application", *Phil. Trans. R. Soc. Long*, vol. B 316, pp. 85-94 (1987).

Pollack et al., "Enzyme Immobilization by Condensation Copolymerization into Cross-Linked Polyacrylamide Gels", *J. Am. Chem. Soc.*, vol. 102, No. 20, pp. 6324-6336 (1980).

Castner et al., "Mass Transport and Reaction Kinetic Parameters Determined Electrochemically for Immobilized Glucose Oxidase", *Biochemistry*, vol. 23, No. 10, pp. 2203-2310 (1984).

Abstract of U.S. Pat. No. 4,193,982, Mar. 18, 1980, Avaremas et al.

Abstract of Brandt, et al., "Covalent attachment of proteins to polysaccharide carriers by means of benzoquinone", *Biochem. Biophys. Acta.* 386(1), 196-202 (1975).

Abstract of Narasimhan et al., "p-Benzoquinone activation of metal oxide electrodes for attachment of enzymes", *Enzyme Microb. Technol.*, 7(6), 28-6 (1985).

Abstract of Ikeda et al., "Glucose oxidase-immobilized benzoquinone-carbon paste electrode as a glucose sensor", *Agric. Biol. Chem.*, 49(2), 541-3 (1985).

Abstract of U.S. Pat. No. 4,581,336, Apr. 8, 1986, Malloy et al.

Abstract of European Patent No. 177,743 A2, Apr. 16, 1986.

Abstract of Bartlett et al., "Modification of glucose oxidase by tetrathiafulvalene", *J. Chem. Soc. Chem. Commun.*, (16) (1990).

Abstract of Albery et al., "Amperometric enzyme electrodes. Part II. Conducting salts as electrode materials for the oxidation of glucose oxidase", *J. Electoanal. Chem. Interfacial Electrochem.*, 194(2), 223-35 (1985).

Yao, "A Chemically-Modified Enzyme Membrane Electrode as an Amperometric Glucose Sensor", *Analytica Chemica Acta*, vol. 148, pp. 27-33 (1983).

Dicks et al., "Ferrocene modified polypyrrole with immobilised glucose oxidase and its application in amperometric glucose microbiosensors", *Ann. Biol. Clin.*, vol. 47, pp. 607-619 (2983).

Yabuki et al., "Electro-conductive Enzyme Membrane", *J. Chem. Soc., Chem. Commun.*, pp. 945-946 (1989).

Trojanowicz et al., "Enzyme Entrapped Polypyrrole Modified Electrode for Flow-Injection Determination of Glucose", *Biosensors and Bioelectronics*, vol. 5, pp. 149-156 (1990).

Degani et al., "Direct Electrical Communication Between Chemically Modified Enzymes and Metal Electrodes. 1. Electron Transfer from Glucose Oxidase to Metal Electrodes via Electron Relays, Bound Covalently to the Enzyme," *Journal of Physical Chemistry*, vol. 91, pp. 1285-1289 (1987).

Degani et al., "Direct Electrical Communication Between Chemically Modified Enzymes and Metal Electrodes. 2. Methods for Bonding Electron-Transfer Relays to Glucose Oxidase and D-Amino-Acid Oxidase," *JACS*, vol. 110, pp. 2615-2620 (1988).

Bartlett et al., "Covalent Binding of Electron Relays to Glucose Oxidase," *J. Chem. Soc., Chem. Commun., pp. 1603-1604 (1987).*

Umana, U.S. Army Research Office Report No. ARO (List continued on next page.)

OTHER PUBLICATIONS 23106.3-LS entitled "Protein-Modified Electrochemically Active Biomaterial Surface", dated Dec. 1988.

Samuels et al., "An Electrode-Supported Oxidation Catalyst Based on Ruthenium (IV). pH 'Encapsulation' in a Polymer Film," *J. Am. Chem. Soc.*, vol. 103, pp. 307-312 (1981).

Denisevich et al., "Unidirectional Current Flow and Charge State Trapping at Redox Polymer Interfaces on Bilayer Electrodes: Principles, Experimental Demonstration, and Theory," *J. Am. Chem. Soc.*, vol. 103, pp. 4727-4737 (1981).

Abruna et al., "Rectifying Interfaces Using Two-Layer Films of Electrochemically Polymerized Vinylpridine and Vinylbipyridine Complexes of Ruthenium and Iron on Electrodes," *J. Am. Chem. Soc.*, vol. 103, pp. 1-5 (1981).

Ellis et al., "Selectivity and Directed Charge Transfer Through an Electroactive Metallopolymer Film," *J. Am. Chem. Soc.*, vol. 103, pp. 7480-7483 (1981).

Gregg et al., "Cross-linked Redox Gels Containing Glucose Oxidase for Amperometric Biosensor Applications", 1990, pp. 258-263.

Coughlan, "Concepts and Approaches to the Understanding of Electron Transfer Processes in Enzymes Containing Multiple Redox Centers", 1980, Chapter 5, *Molybdenum-Containing Enzymes*, pp. 187-220.

Nagy et al., "A New Type of Enzyme Electrode: The Ascorbic Acid Eliminator Electrode", *Life Sciences*, vol. 31, pp. 2611-2616, Pergamon Press, 1982.

Heller, A., "Electrical Wiring of Redox Enzymes", Reprinted from *Accounts of Chemical Research*, vol. 23, No. 5, 1990 (pp. 128-134).

Japanese Patent No. 03028752 A2 to Omochi et al., "Method for Manufacture of an Electrode Containing Immobilized Enzyme and Interfering-Substance—Eliminating Membrane," (Abstract), *Chemical Abstracts*, 114(21):203143u, 1991.

German patent No. 3934299 C1, "Enzyme Electrodes Containing Oxidase and Peroxidase" to Schmid et al., (Abstract), *Chemical Abstracts*, 114(23):225208w, 1991.

Japanese Patent Application No. 02310457 A2; "Enzyme Biosensor for Micro Analysis of Body Fluid" (Abstract), *Chemical Abstracts*, 114(21):203111a, 1991.

ELECTRODE AND METHOD FOR THE DETECTION OF HYDROGEN PEROXIDE

This is a continuation-in-part of copending patent application U.S. Ser. No. 389,226 filed Aug. 2, 1989, now U.S. Pat. No. 5,262,035.

FIELD OF THE INVENTION

The present invention relates to an amperometric biosensor or electrode and method for the detection of hydrogen peroxide, NADH or NADPH with high sensitivity. More specifically, this invention is drawn to an electrode having a surface substantially covered with a three-dimensional redox polymer network in which a peroxidase is immobilized, preferably chemically bound.

BACKGROUND OF THE INVENTION

The assay of hydrogen peroxide is relevant to the assay of biochemicals that are oxidized in enzyme catalyzed reactions by molecular oxygen where $O_2$ is reduced to hydrogen peroxide. The hydrogen peroxide is generally assayed spectrophotometrically or electrochemically. An electrochemical assay for $H_2O_2$ may involve electrooxidation of $H_2O_2$, usually near $+0.7V$ (SCE), to $O_2$ or electroreduction, near 0.0V (SCE), to $H_2O$ (Hall, Biosensors, Prentice Hall, Englewood Cliffs, NJ, 1991, p. 16, 135, 221, 224, 283–4; Cass, Biosensors: A Practical Approach, Oxford Univ. Press, 1990, pp. 33, 34)

Detection and quantification of a substantial number of biochemicals is also accomplished by amperometric assay relying on the selective electrooxidation of NADH and NADPH as co-factors of relevant enzymes. The electrooxidation products $NAD^+$ or $NADP^+$ can be enzymatically re-reduced and detected by electrocatalytic enzyme electrodes.

$$NAD(P)H \rightarrow NAD(P)^+ + 2e^- + H^+ \tag{1}$$

The reversible potential of the $NADH/NAD^+$ couple is $-0.55V$ (SCE) at pH7 (McGilvery, Biochemistry-A Functional Approach, W.B. Saunders & Co., Philadelphia, 1983, p. 404). Because this reaction involves the concerted transfer of two electrons and a proton, it is usually slow, proceeding only at high overpotentials to achieve practical rates on most electrodes. At these high overpotentials, reaction products of NAD(P)H and other constituents of biological fluids interfere with amperometric assays of NAD(P)H (Moiroux and Elving, Anal. Chem., 1979, 51:346; Blaedel and Jenkins, Anal. Chem., 1975, 47:1337).

Because of this problem, electrodes were developed on which the conversion of $NAD(P)H$ to $NAD(P)^+$ proceeded rapidly at low overpotential (DeGrand and Miller, J. Am. Chem. Soc., 1980, 102:5728–32; Kitani et al., J. Am. Chem. Soc., 1981, 103:7636–41; Fukui et al., J. Am. Chem. Soc., 1982, 104:28; Lau and Miller, J. Am. Chem. Soc., 1983, 105:5271; Gorton et al., Anal. Chem. Acta., 1991, 250:203–48; Cenas et al., J. Electroanal. Chem. Interfacial Electrochem, 1985, 189:163; Kulys, Biosensors, 1986, 2:3). The most successful of these electrodes utilized electrode-bound, electrode-adsorbed or freely diffusing mediators having quinoid structures in their oxidized state (Gorton et al. 1991; Cenas, 1985; Kulys, 1986; Gorton et al. 1984, J. Electroanal. Chem. Interfacial Electrochem, 1984, 161:103; Persson and Gorton, J. Electroanal. Chem. Interfacial Electrochem, 1990, 292:115; Bremle et al., Electroanalysis, 1991, 3:77–86). The quinoids (Q) effectively catalyze conversion of NAD(P)H to $NAD(P)^+$ at potentials near 0.0V (SEC).

$$Q^+ + NAD(P)H \rightarrow QH + NAD^+ \tag{2}$$

$$QH + O_2 + H^+ \rightarrow Q^+ + H_2O_2 \tag{3}$$

In such electrodes, two electrons and a proton are transferred from NAD(P)H to a quinoid mediator (Reaction 2). A particularly effective mediator is water-soluble 5-methyl-phenazonium cation ($PMS^+$) which is quantitatively reduced by NAD(P)H to 5-methylphenazine (PMSH). PMSH is next reoxidized to $PMS^+$ by dissolved molecular oxygen which is, in turn, reduced to $H_2O_2$ (Reaction 3). In this reaction, each mole of NAD(P)H produces one mole of $H_2O_2$ in the presence of dissolved molecular oxygen.

Previously reported schemes for the detection of NADH and NADPH have amperometrically sensed the L depletion of oxygen (Polster and Schmidt, Talanta, 1989, 36:864–866; Huck et al., Analyst, 1984, 109:147–150) or have spectrophotometrically measured the $H_2O_2$ generated (Williams et al., Anal. Chem., 1976, 48:1481–84; Europ. pat. Appl. EP 317070, 1989; Europ. Pat. Appl. EP 285998, 1989) by these reactions.

Such indirect detection methods suffer problems of interference by other constituents in the test sample, and/or lack the sensitivity of a useful amperometric biosensor.

It would be highly desirable to provide an amperometric biosensor for the detection of $H_2O_2$, NADH and NADPH which is highly sensitive and which is not significantly hampered by interfering substances in a test sample.

SUMMARY OF THE INVENTION

The present invention solves the problems of prior art amperometric biosensors by providing a biosensor which is highly sensitive and which accurately measures $H_2O_2$, NADH or NADPH in a biological sample. The electrode and method of the present invention accurately and with great sensitivity measures hydrogen peroxide directly by the reaction:

$$H_2O_2 + 2e^- + 2H^+ \rightarrow 2H_2O \tag{4}$$

The inventive biosensor includes an electrode which is substantially covered by a three-dimensional redox polymer network in which a peroxidase or peroxidase-like molecule is immobilized, and preferably is chemically bound. This redox polymer network electrically connects, i.e., "wires" redox centers of peroxidase to the electrode.

Thus, the following sequence of electron transfer becomes operative: $H_2O_2$ oxidizes peroxidase and is reduced to water; peroxidase is reduced by the 3-dimensional redox polymer network, which is oxidized; and the oxidized redox polymer network is electroreduced by electrons originating at the electrode. The net reaction is the electrocatalytic reduction of $H_2O_2$ to water. This reaction proceeds throughout the 3-dimensional network, not only at the electrode surface, wherefor the current density and sensitivity, i.e., the transduction of $H_2O_2$ flux to the network to an electrical current, are high.

Furthermore, because no diffusional electron shuttling mediators that may be lost by random diffusion to the entire volume of the solution prior to reaching the electrode are involved in the transport of charge, the current efficiency of the $H_2O_2$ electroreduction reaction is also high. Electrons originating at the electrode are thus efficiently relayed through the redox polymer network to the bound peroxidase. In the presence of $H_2O_2$, a current flows. $H_2O_2$ is a molecule that oxidizes redox centers of peroxidase, i.e., depletes these of electrons. The electrons transferred from the peroxidase to $H_2O_2$ reduce $H_2O_2$ to $H_2O$. This transfer of electrons represents an electrical current which is proportional to the concentration of $H_2O_2$ in the test solution, unless the H20z concentration exceeds the peroxidase inhibiting concentration, near $3 \times 10^{-4}M$ for horseradish peroxidase.

Such direct detection allows a rapid and highly sensitive assay for hydrogen peroxide, and also permits a rapid and highly sensitive detection and quantification assay for the cofactors NADH and NADPH and substrates of enzymes which utilize these cofactors.

DETAILED DESCRIPTION OF THE INVENTION

Figures 1, 2:
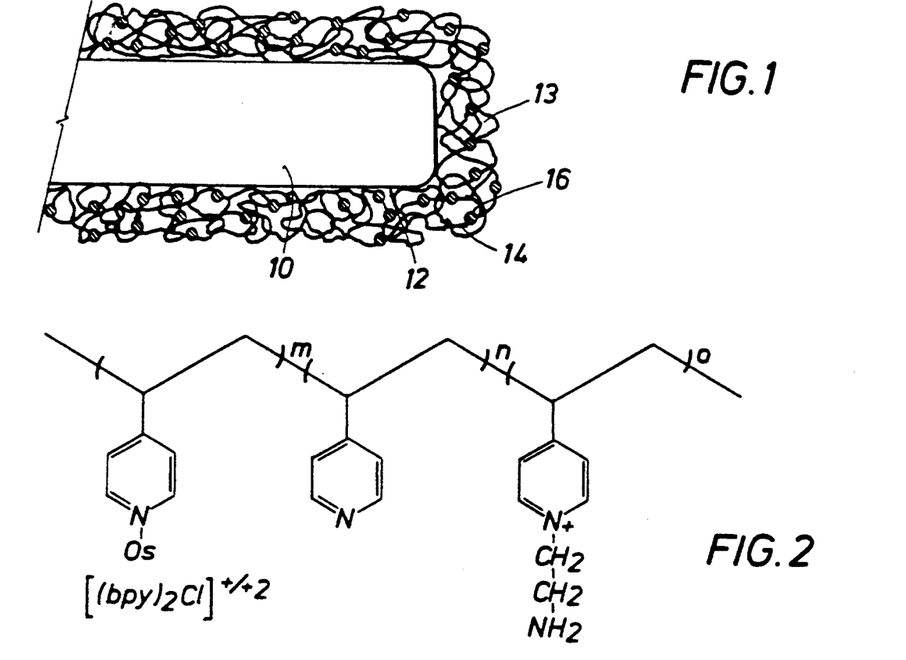
FIG. 1 is a schematic diagram of an electrode of the present invention.
FIG. 2 is a diagrammatic representation of the structure of Polymer I (PVP-Os-NH$_2$).

As shown in FIG. 1, a biosensor of the present invention includes an electrode 10 having a testing surface 12. The surface 12 is substantially covered with a three-dimensional redox polymer 14 in which peroxidase 16 or a peroxidase-like molecule is immobilized, preferably chemically bound, to the redox polymer. The three-dimensional redox polymer network 14 electrically connects the electrode 10 to the peroxidase enzyme 16. The electrode 10 may be formed of any material known for the manufacture of biosensing electrodes. Preferably the electrode is formed of a solid material, e.g., gold or glassy carbon. Additional suitable electrode materials include graphite, platinum, palladium, tin oxide, and conducting organic salts.

The three-dimensional redox polymer includes at least two components. At least one of these components comprises a redox compound, and at least one other component comprises a peroxidase, or peroxidase-like molecule. The three-dimensional molecular structure has multiple redox centers and has the peroxidase enzyme chemically bound within.

The term "immobilized" is meant to describe a peroxidase enzyme or a peroxidase-like molecule which is retained within the redox polymer network and does not freely diffuse away. The peroxidase may be entrapped, but is preferably chemically bound, and more preferably covalently bonded to the redox polymer.

The peroxidase may be horseradish peroxidase or a faster peroxidase such as the fungal peroxidase from Arthromyces ramosus. Alternatively, a peroxidase-like molecule such as a heme-containing molecule, e.g., an imidazole, vinyl imidazole or polyvinyl imidazole complex of a water-soluble hemin derivative.

As used herein, the term "peroxidase" includes peroxidase-like molecules. The term "peroxidase-like molecules" is meant to define molecules which include a redox center that is oxidized by $H_2O_2$ and is electrochemically reduced by electron transfer from an electrode.

The term "redox compound" is used herein to mean a compound that can be oxidized and reduced. The redox compound may have one or more functions that are reducible and oxidizable. Further, the term "redox compound" means a compound which contains one or more redox centers, "redox center" meaning a chemical function that accepts and transfers electrons.

The redox compounds, or redox centers contained within compounds useful in this invention may be organic or inorganic. Transition metal complexes with organic ligands such as, for example, bipyridine and the like, are preferred as redox centers because of their chemical stability and various oxidation states and their facial electron transfer kinetics. Examples of such complexes include polypyridine complexes of dior trivalent osmium ions. However, a number of organic redox centers may also be employed. Various derivatives of viologen (N,N'-bis alkyl-4,4'-bipyridine) constitute typical examples of this class. A number of preferred cross-linkable compounds containing redox active centers are known. Some of these compounds require only the addition of enzymes to form 3-dimensional crosslinked films, i.e., the enzyme is the only required crosslinking agent. Other compounds do not directly react with chemical functions present on the enzyme and thus require a separate crosslinking agent to form the 3-dimensional network.

A preferred redox polymer complex for use in the present invention is Polymer I, PVP-Os-NH$_2$, shown in FIG. 2. To prepare Polymer I, poly(vinylpyridine) is complexed with [osmium bis(2,2'-bipyridine) dichloride] to yield the polymer abbreviated [Os(bpy)$_2$Cl$_2$]. This polymer (PVP-Os) is then quaternized, e.g., with bromoethylamine hydrobromide to form a very hydrophilic, crosslinkable redox polymer, containing pendant ethylamine groups (PVP-Os-NH$_2$) as shown in FIG. 2.

Figure 3:
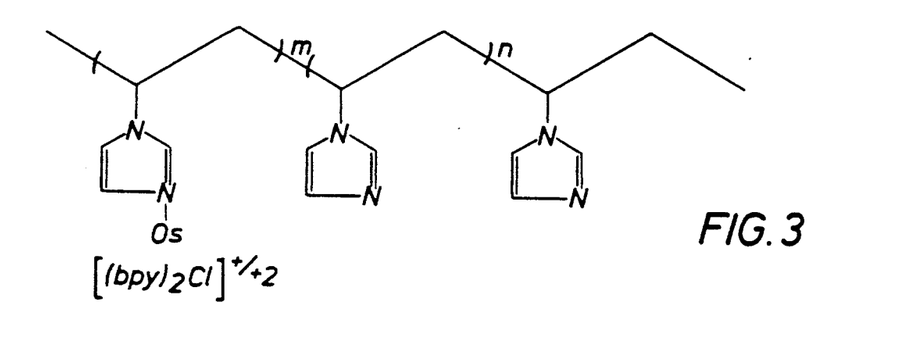
FIG. 3 is a diagrammatic representation of the structure of Polymer II (PVI-Os).
Figure 4:
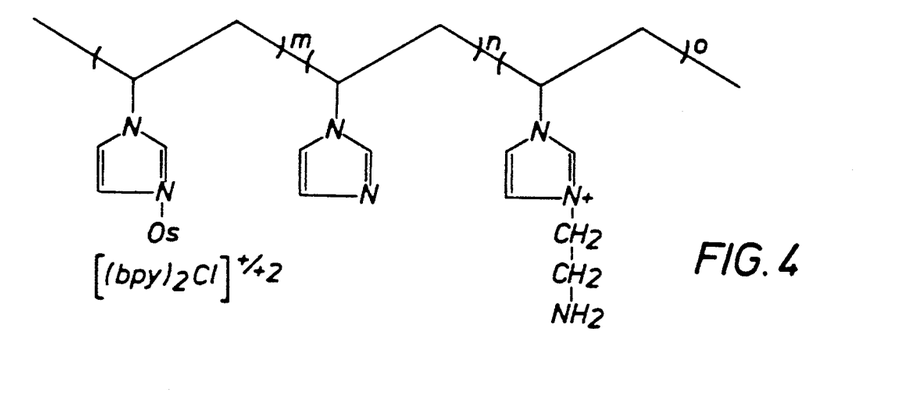
FIG. 4 is a diagrammatic representation of the structure of Polymer III (PVP-Os-NH$_2$).

Novel redox polymers useful in this invention also include derivatives of poly(N-vinyl imidazole) (PVI) complexed with [Os(bpy)$_2$Cl]$^{+/2+}$ forming PVI-Os (Polymer II), shown, for example, in FIG. 3. PVI-Os is by itself a crosslinkable redox polymer, but may also be quaternized to form PVI-Os-NH$_2$ (Polymer III) for additional crosslinking sites (see FIG. 4).

In a preferred embodiment, the three-dimensional redox polymer network includes a peroxidase enzyme, a cross-linking agent, and a cross-linkable compound capable of reacting with the cross-linking agent and the peroxidase. Either the cross-linkable compound or the cross-linking agent, or both, contain at least one but preferably multiple redox centers.

Preferred cross-linking agents are water soluble compounds that react under conditions where enzymes are stable, that is, in aqueous solutions, approximately at pH 3-9 and at 0°-50° C. Included in this category of cross-linking agents are multi-functional epoxides such as polyethylene glycol diglycidyl ether (PEGDGE), carbodiimides, and di and poly aldehydes, imidoesters, and N-hydroxysuccinimid esters. A number of reagents with limited solubility in water may also be used by dissolving them in a water-miscible organic solvent such as acetone, methanol, acetonitrile or dimethylformamide. Included in this category are reagents such as cyanuric chloride, tetrachlorobenzoquinone, and tetracyanoquinodimethane. These reagents may react with one or more types of functions including amides, alcohols, thiols and carboxylic acids which may be present on the surface of enzymes and which may also be included in the structure of the redox compound.

Additional crosslinkers which may be used in preparing the electrodes of the present invention include di, tri, and poly aziridines, e.g., Preferred crosslinkable compounds are hydrophilic, containing chemical groups such as alcohols, carboxylic acids, amines, sulfonates, sulfates, phosphates, and phosphonates. Such groups tend to promote the solubility of the components in water which facilitates contact with the water soluble enzymes. Such groups may also improve the stability of the immobilized enzyme against denaturation.

To form the inventive electrodes, the components of the three-dimensional redox polymer network are mixed together under appropriate conditions such that a chemical reaction takes place resulting in the formation of a three-dimensional redox polymer having peroxidase enzyme bound within a three-dimensional redox polymer network.

Mixture of peroxidase and the various polymer components in a common solution is followed by the application of the solution to an electrode surface. Various application methods may be used, including the addition of drops of the solution onto the electrode surface, dip coating, spin coating, or spraying the solution onto the electrode surface. The application step is followed by a curing or setting step, involving drying in air or vacuum. Alternatively, the process may involve the addition of the enzyme and polymer components in separate solutions to the surface of the electrode, mixing, and then curing or setting in air or vacuum.

When such materials are coated onto an electrode surface, the three-dimensional molecular structure which results provides electrical contact between the surface of the electrode and the included peroxidase enzyme.

Figure 5:
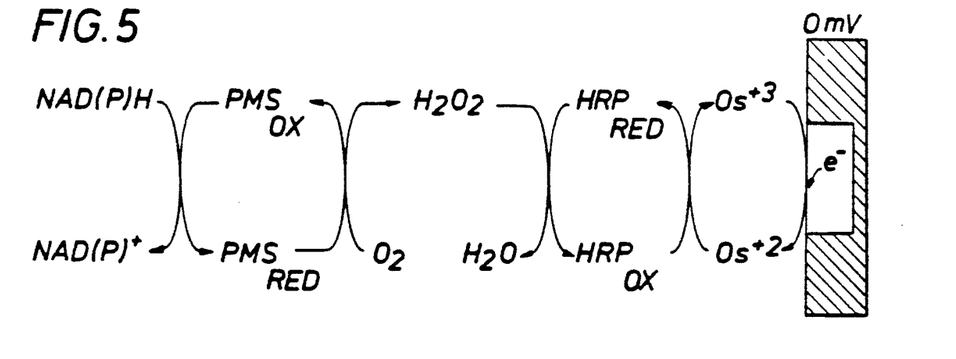
FIG. 5 is a diagrammatic representation of electron transfer in an electrode of the present invention.

In the method of the present invention, the inventive electrode is used to directly detect H$_2$O$_2$ in a test sample. In this method, electrons generated at the electrode are relayed to the peroxidase enzyme through the redox polymer (e.g., epoxy) network to which the peroxidase is chemically bound. As shown in FIG. 5, electrons are relayed to the peroxidase enzyme which is electroreduced at potentials negative of 0.35V (SCE), generally 0.0V (SCE). In the presence of H$_2$O$_2$ in the test sample, the electrons are then transferred from the reduced peroxidase to hydrogen peroxide resulting in the generation of water (see reaction 4). The transfer of electrons from the electrode through the polymer network and through peroxidase to hydrogen peroxide implies the flow of an electrical current. This current is a function of the concentration of H$_2$O$_2$ in the test solution. By this method, H$_2$O$_2$ is detected with approximately 1Acm$^{-2}$M$^{-1}$ sensitivity.

Because NAD(P)H concentrations are stoichiometrically translated to H$_2$O$_2$ through the reactions discussed previously (2)(3), these cofactors are also detected by this method at the same potential with the same sensitivity. In addition, substrates whose enzyme catalyzed reactions generate H$_2$O$_2$ or NAD(P)H may be assayed using the biosensor and method of the present invention with a related sensitivity.

Figure 6:
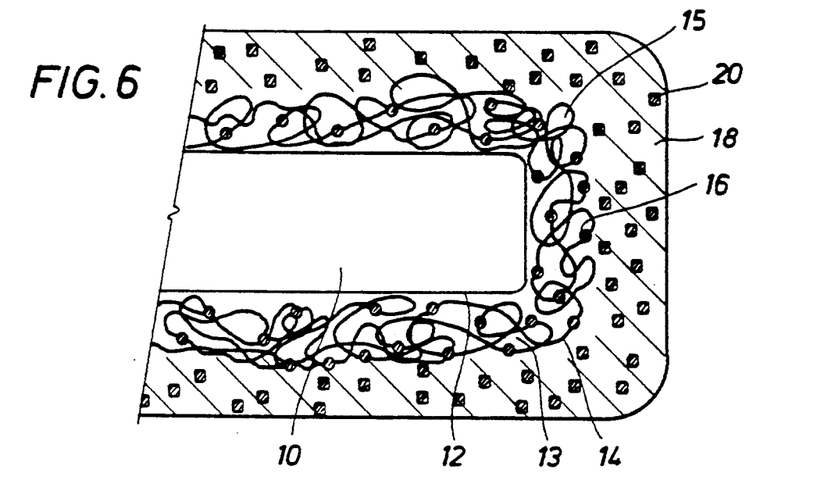
FIG. 6 is a schematic diagram of a bi-layer electrode of the present invention.

In an alternative preferred embodiment, as shown in FIG. 6, the biosensor of the present invention may include two enzyme-containing layers on the electrode. In the immediate proximity of the electrical conductor, e.g., the electrode 10, is a first, peroxidase-containing layer 15, which, as discussed for the peroxidase-containing electrodes above, is electrically connected, i.e., "wired" through a three-dimensional redox polymer network to the electrode. A second enzyme layer 18 is located between the peroxidase layer 15 and the solution to be tested, and contains an enzyme 20 which accelerates a reaction of which hydrogen peroxide is product. Examples of such an enzyme 20 include glucose oxidase which accelerates oxidation of glucose by oxygen to gluconolactone and hydrogen peroxide.

Suitable enzymes for use as the second enzyme 20 include those which induce reaction of a substrate whose detection is sought in a biological sample, the reaction generating hydrogen peroxide which may be detected on the peroxidase portion of the electrode. Examples of such enzymes include glucose oxidase, amino acid oxidase, cholesterol oxidase, theophylline oxidase, sarcosine oxidase and the like.

This bilayer peroxidase biosensor permits detection of biological substrates by a reaction induced by the first enzyme 20 which generates hydrogen peroxide. $H_2O_2$ is then efficiently electroreduced at 0.0V (SEC) and detected by the peroxidase electrode system described above. The resulting sensitivity is very high and proceeds with little interference by contaminating biological species which are not electroreduced or electrooxidized at 0.0V (SCE).

In the bilayer peroxidase biosensor, the peroxidase enzyme 16 and the second enzyme 20 are electrically isolated from each other, i.e., the second enzyme 20 is not electrically connected to the electrode, and not electrically connected to the redox polymer network to which the peroxidase is bound. Such electrical isolation may be achieved by construction of a sensor where an outer layer containing the second enzyme 20 is physically separated from an inner layer containing the peroxidase-redox polymer network.

Alternatively, a single layer structure containing both enzymes may be used. This single layer includes in the electrode-contacting "wired" peroxidase layer also the second enzyme 20, whose redox centers are nevertheless insulated from the redox network, e.g., by a protein or glycoprotein shell, such that the second enzyme is not sufficiently contacted, i.e., is not "wired" by the three-dimensional redox network. Such insulation prevents reduction of the second enzyme by the network or its oxidation by $H_2O_2$-oxidized peroxidase. Upon reacting with $O_2$ after being reduced by its substrate, the second enzyme 20 generates hydrogen peroxide, which oxidizes the "wired" peroxidase network and is thus sensed.

In another embodiment, the $H_2O_2$ producing second enzyme 20 may be electrically isolated from the 3-dimensional redox network and bound peroxidase by maintaining the network at a potential where the second enzyme is not oxidized or reduced.

"Electrical contact" is defined as the situation where current will flow in the external circuit as a result of oxidation or reduction reaction in one or more layers of the sensor.

"Electrical isolation" and "Electrical insulation" describe the situation where a current in the external circuit will not flow as a result oxidation or reduction reaction in the isolated or insulated layer.

Electrical isolation or insulation of the second enzyme 20 from the 3-dimensional redox polymer 14 and peroxidase 16 permits both enzymes to be included in the same layer, e.g., $H_2O_2$ producing second enzyme 20 may be embedded in the 3-dimensional redox polymer network 12. At the operating potential of the electrode, e.g., 0.0V (SCE) current is produced only by flow of electrons from the electrode to hydrogen peroxide and little or no current results from direct reduction or oxidation of the $H_2O_2$ producing second enzyme (20).

EXAMPLES

The following examples are designed to illustrate certain aspects of the present invention. The examples are not intended to be comprehensive of all features and all embodiments of the present invention, and should not be construed as limiting the claims presented herein.

EXAMPLE 1

Production of $H_2O_2$ sensing electrodes

Rotating disk electrodes were made of vitreous carbon rods, one centimeter in length, three millimeters in diameter. The disk electrodes were press-fitted into one end of a Teflon sleeve. The opposite end of the sleeve contained a press-fitted stainless steel rod threaded to match a rotator. Electrical contact between the vitreous carbon and stainless steel rods was made with a silver epoxy EPO-TEK H20E (Epoxy Technology, Inc., Billerica, MA). The electrodes were polished first with a 6 $\mu M$ then with 1 $\mu M$ diamond suspension, followed by 0.3 $\mu M$ alumina. After each polishing step, the electrodes were sonicated for three to six minutes in the deionized water.

Horseradish peroxidase (HRP) (2 mg) (Sigma P-8375 Type VI, 260 Units/mg) was dissolved in 100 $\mu L$ of 0.1M sodium bicarbonate solution. After the addition of 50 $\mu L$ of 12 mg/ml sodium periodate, the enzyme solution was incubated in the dark for 2.3 hours. A 10 mg/ml solution of Polymer I, an osmium redox polyamine, synthesized as described in Gregg and Heller, *J. Phys. Chem.*, 1991, 95:5970-75, and shown in FIG. 2. was used to dilute aliquots of the enzyme solution resulting in enzyme:Polymer I solutions having various ratios (1:5, 1:10, 1:50, 1:100).

A volume of one microliter of the enzyme:Polymer I (PVP-Os-NH2) solution was applied to the polished vitreous carbon surface. The electrodes were allowed to partially dry for five to fifteen minutes, after which one microliter of a 1 mg/ml solution of poly(ethylene glycol 600 diglycidyl ether), technical grade (PEGDE) (Poly Sciences, No. 8211) was applied. The electrodes were then cured in water-saturated air at room temperature for at least four hours.

Electrodes were also prepared by coimmobilizing HRP previously oxidized with $NaIO_4$ with a polyamine that had no redox centers. This polyamine was obtained by reacting polyvinylpyridine (PVP) (MW 60,000) with 2-bromoethylamine to form the pyridinium-N-ethylamine derivative, i.e., the polymer was Polymer I without $[Os(bpy)_2Cl]^{+/2+}$ redox centers. The HRP was crosslinked to the polyamine using PEGDE through the above-described process.

EXAMPLE 2

Use of $H_2O_2$ Sensing Electrodes

The electrodes prepared in Example I were exposed to test solutions containing $H_2O_2$. in modified Dulbecco's buffer (PBS) pH 7.4. Unless otherwise indicated, the solutions were well aerated. All mediator solutions were made daily and protected from light until used. Potentials were referenced to a saturated calomel electrode (SCE). A platinum wire was used as the counter electrode. The chronoamperometric experiments were performed on an EG and G potentiostat/galvanostat Model 173 and recorded on a Kipp and Zonen XY recorder Model BD91. The cyclic voltammograms were run on an EG and G potentiostat/galvanostat Model 273A and computer recorded. The rotator used was a Pine Instruments AFMSRX with an ACMDI 1906C shaft.

Figure 7:
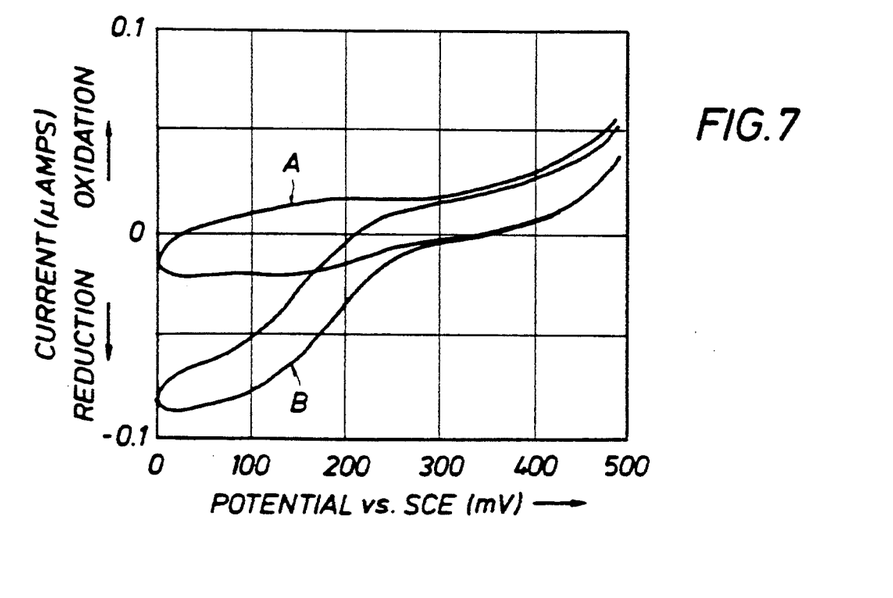
FIG. 7 is a graphical depiction of electroreduction of $H_2O_2$ on an electrode having a 3-dimensional polymer network which lacks redox centers. Curve A is measured without $H_2O_2$; curve B is measured with $10^{-4}M$ $H_2O_2$.
Figure 8:
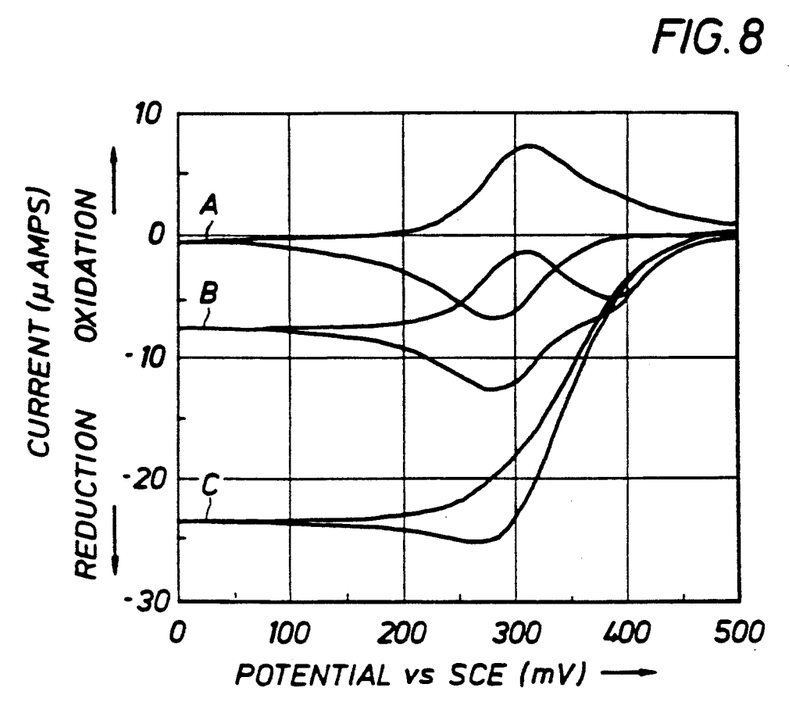
FIG. 8 is a graphical depiction of electroreduction of $H_2O_2$ on a rotating electrode having a 3-dimensional redox polymer network. Curve "A" is measured without $H_2O_2$ at 500 rpm; Curve "B" is measured with $10^{-4}M$ $H_2O_2$ at 500 rpm; Curve "C" is measured with $5 \times 10^{-4}M$ $H_2O_2$ at 2000 rpm.

Electroreduction of $H_2O_2$ was observed on electrodes containing horseradish peroxidase (HRP) chemically bonded in the epoxy network of both the polyamine without redox centers (FIG. 7) or the polyamine containing osmium redox centers (FIG. 8). In the absence of the redox centers, some reduction took place at potentials negative of 0.2V(SCE). In the presence of $1 \times 10^{-4}M$ $H_2O_2$, a plateau of approximately 1 $\mu Acm^{-2}$ was reached near 0.1V(SCE) (FIG. 7). In contrast, using the inventive electrode having a redox epoxy network with multiple osmium redox centers, the current density at 0.0V (SCE) increased by two orders of magnitude to about 100 $\mu Acm^{-2}$. Furthermore, $H_2O_2$ electroreduction was observed even at a potential as oxidizing as +0.45V (SCE) and steady-state electroreduction current plateaus were observed already at a potential as oxidizing as +0.3V (SCE), as shown in FIG. 8.

In these electrodes, the catalytic $H_2O_2$ electroreduction current density was relatively independent of the HRP:Polymer I ratio. A series of electrodes was examined. These were prepared as described for Example I, but with varied ratios of peroxidase:polymer.

Figure 9:
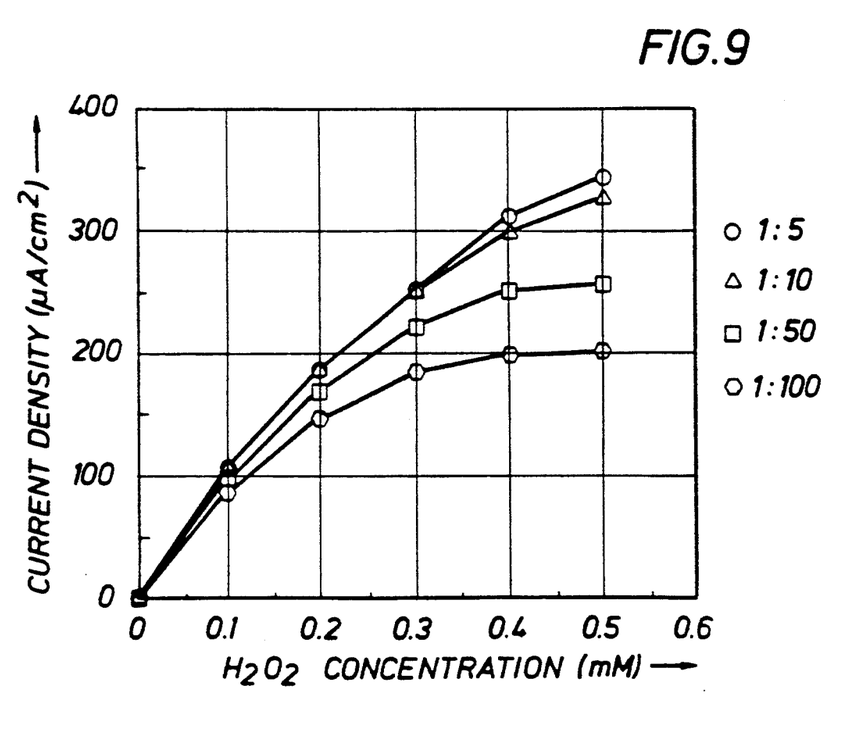
FIG. 9 is a graphical depiction of electroreduction of $H_2O_2$ on electrodes formed with varied ratios of HRP: Polymer I.

The catalytic $H_2O_2$ electro-reduction current density of these electrodes was measured, and the results are shown in FIG. 9. The current density generated was nearly independent of the HRP:polymer ratio at low $H_2O_2$ concentrations (e.g. less than $1 \times 10^{-4}M$). At higher $H_2O_2$ concentrations, the current density increased as the polymer network became richer in HRP, up to a ratio of approximately 1:5. Current densities of electrodes containing an HRP:polymer I ratio of 1:10 and 1:5 did not differ greatly. For electrodes having a 1:5 HRP:Polymer I ratio, the sensitivity of the electrode in the concentration range of 0–1 33 $10^{-4}M$ $H_2O_2$ was $1Acm^{-2}M^{-1}$, i.e. the current density at $1 \times 10^{-4}M$ $H_2O_2$ was 100 $\mu Acm^{-2}$. When the $H_2O_2$ concentration exceeded 0.25mM, the current was time dependent and decayed, presumably because of substrate inhibition of HRP. Control electrodes made with a Polymer I network in the absence of HRP showed no measurable $H_2O_2$ response.

Figure 10:
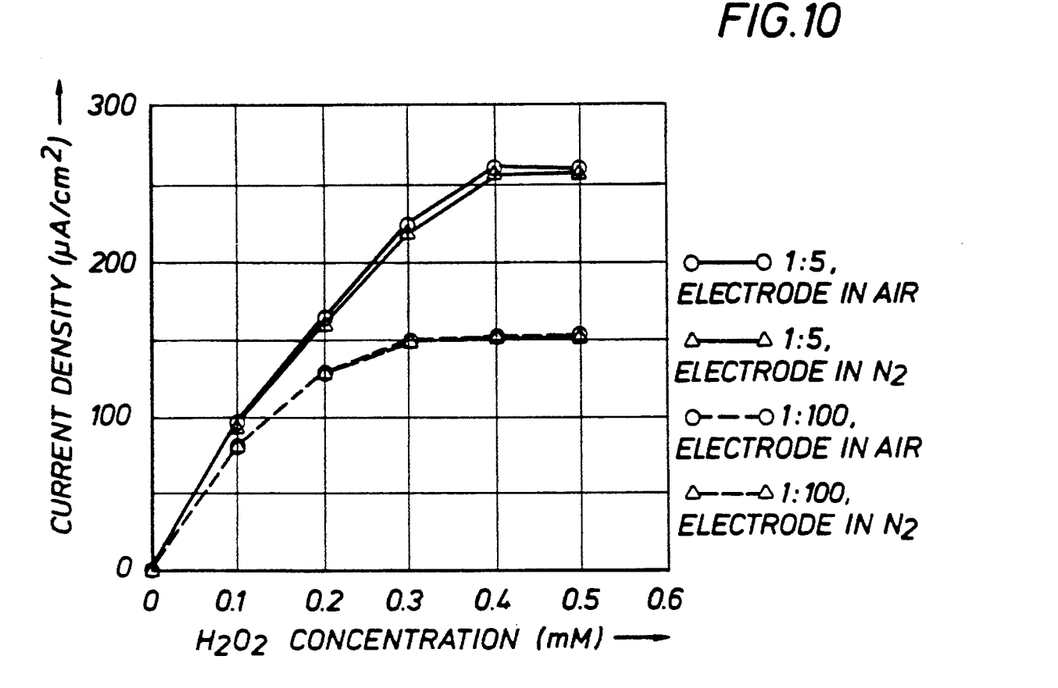
FIG. 10 is a graphical depiction of electroreduction of $H_2O_2$ on electrodes of the present invention in nitrogen-purged and air-saturated solutions.

FIG. 10 illustrates the insensitivity of the electrodes of the present invention to the partial pressure of oxygen, a feature of particular importance in the analysis of venous and arterial blood constituents and of constituents of bioreactors. In FIG. 10, measurements in air-saturated solutions are shown in open circles and those in the $N_2$-purged solutions are shown in closed circles. No measurable difference was seen between the calibration curves of the 1:100 (HRP:Polymer I) electrode in nitrogen-purged or air-saturated solutions. For the 1:5 (HRP:Polymer I) electrode there was a marginal difference, with readings in air exceeding those in nitrogen by less than 2%.

Figure 11:
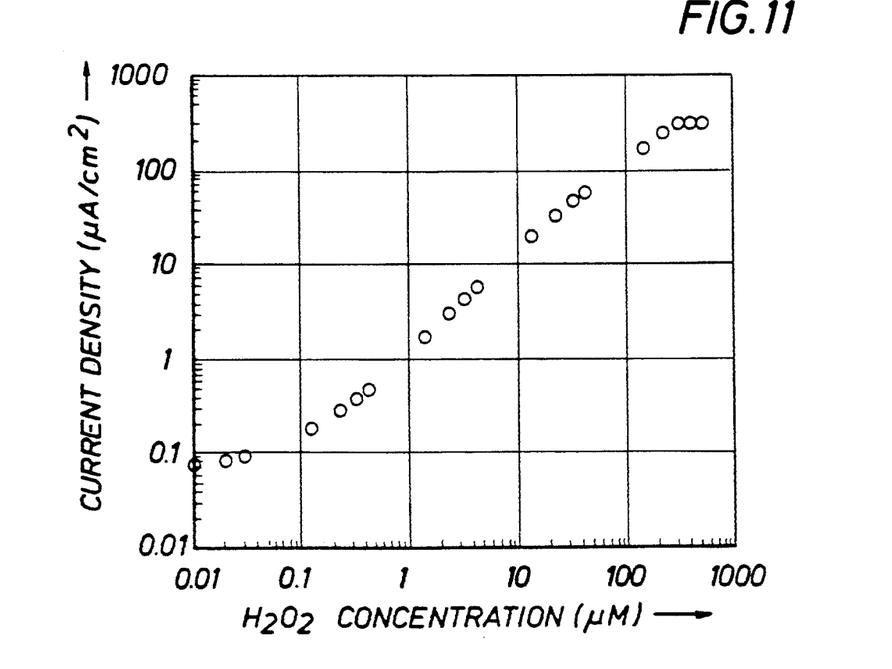
FIG. 11 is a graphical depiction of electroreduction of $H_2O_2$ on electrodes of the present invention at various concentrations of $H_2O_2$.
Figures 12A, 12C:
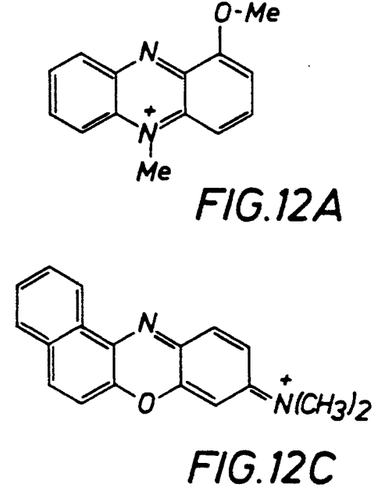
FIG. 12A to FIG. 12J display the chemical structure of heterocyclic quinoid mediators useful in the method of the present invention.
Figures 12B, 12D:
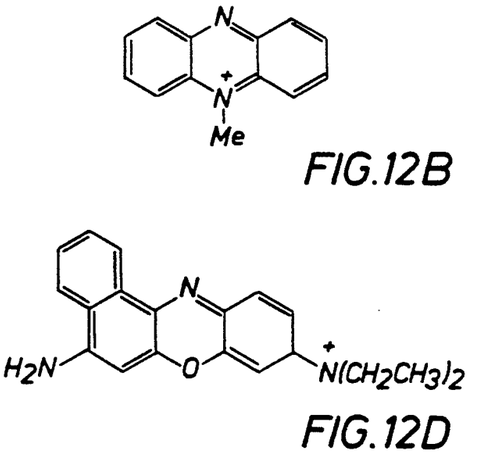
Figure 12E:
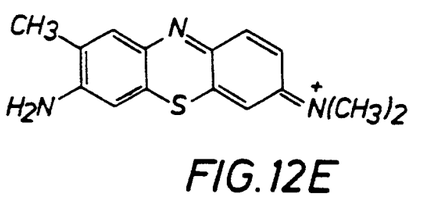
Figure 12F:
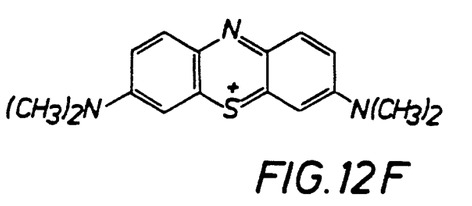
Figure 12G:
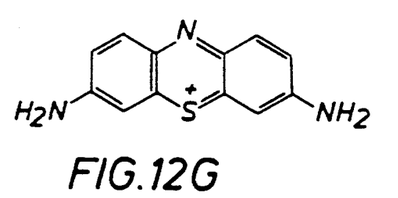
Figure 12H:
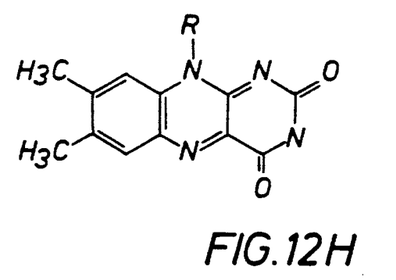
Figure 12I:
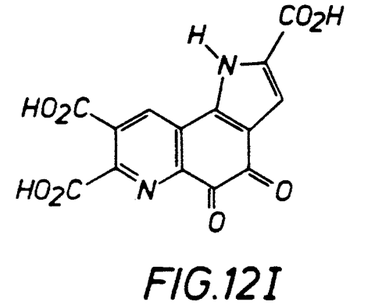
Figure 12J:
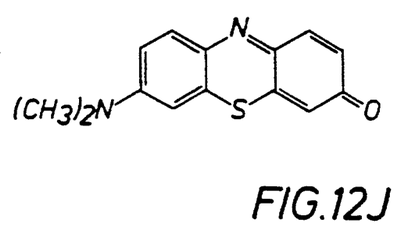

The dynamic range of the HRP electrode was demonstrated using the electrode containing HRP in a ratio of 1:5 HRP:Polymer I. When this electrode was contacted with test solutions containing varied concentrations of $H_2O_2$ over a range of three orders of magnitude from about $1 \times 10^{-7}M$ to about $1 \times 10^{-4}M$, the current density increased linearly with $H_2O_2$ concentrations (correlation coefficient 0.997; slope $1Acm^{-2}M^{-1}$), as shown in FIG. 11. At low concentrations, the time-response of the electrodes was slow. Following an $H_2O_2$ injection raising the concentration from 0.0M to $1 \times 10^{-7}M$, the current reached a steady state in approximately ten minutes. At higher concentrations, the response time was faster, e.g., two minutes for $1 \times 10^{-5}M$ $H_2O_2$. The noise equivalent $H_2O_2$ concentration was approximately 3mM, i.e., at $1 \times 10^{-8}M$ $H_2O_2$ the signal to noise ratio was approximately three. The background current, measured after the electrode was allowed to stabilize for 30 minutes, was $70nAcm^{-2}$ at 0.0V (SCE).

EXAMPLE 3

Use of "Wired" HRP Electrodes to Sense NAD(P)H

The electrodes prepared as described in Example 1, when immersed in a solution to which either NADH or NADPH was added, showed no change in background current at 0.0V (SCE). However, when a heterocyclic quinoid was added to the test solution, an NAD(P)H concentration-dependent cathodic current was observed.

The structures of useful heterocyclic quinoids are shown in FIG. 12A to FIG. 12J, with the relative effectiveness of mediators in the generation of $H_2O_2$ reflected in the order of their listing. Addition of any of these mediators to the test solution at less than 10mM concentrations did not change the observed current.

Figure 13:
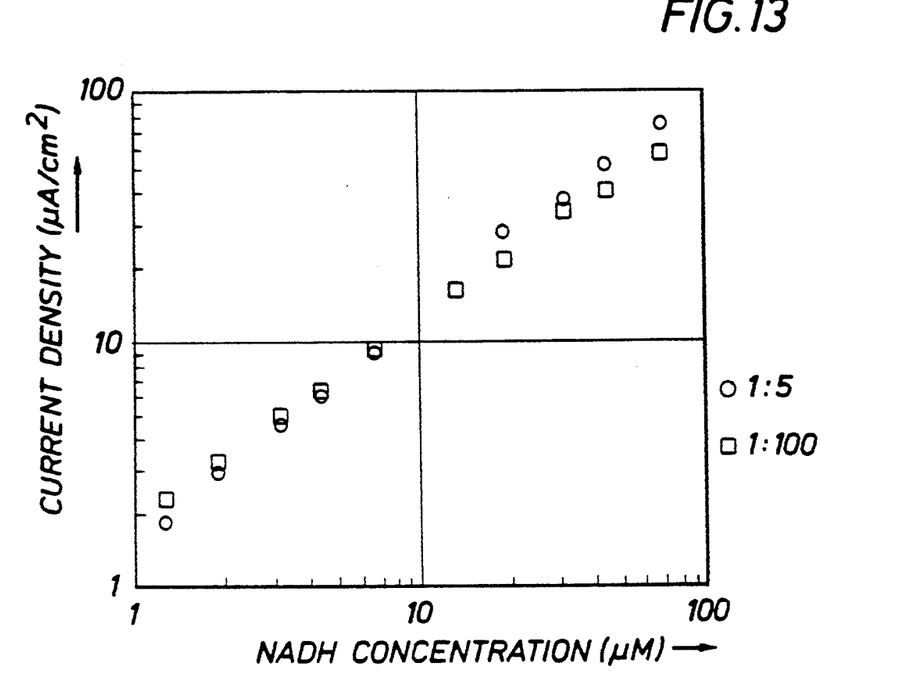
FIG. 13 is a graphical depiction of electroreduction of $H_2O_2$ on electrodes of the present invention in a test solution containing 5-methylphenazonium methylsulfate and in response to NADH.

As shown in FIG. 13, a linear variations in current density with NADH concentration was observed when HRP electrodes containing a ratio of HRP:polymer of 1:5 and 1:100 were immersed in test solutions containing 1.6mM 5-methylphenazonium methylsulfate (PMS+) and varied concentrations of NADH. The NADH concentration dependence of the current density remained linear through a range of NADH concentrations from 1–100 $\mu M$ and the slope, i.e., sensitivity, was $1Acm^{-2}M^{-1}$, similar to that previously obtained for $H_2O_2$ concentrations.

Figure 14:
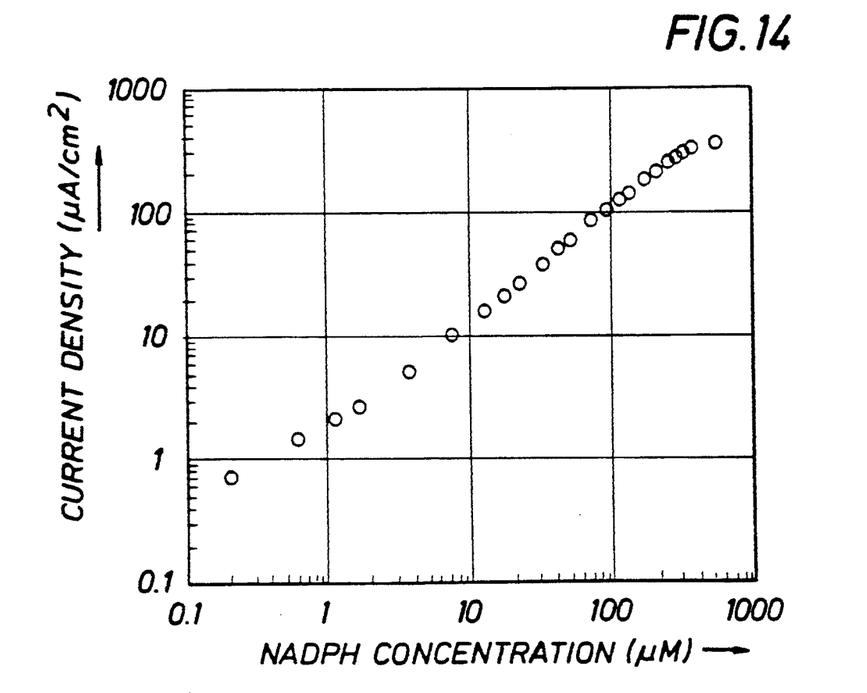
FIG. 14 is a graphical depiction of electroreduction of H202 on electrodes of the present invention in a test solution containing 5-methylphenazonium methylsulfate and in response to NADPH.

This experiment was repeated using an electrode having a ratio of 1:5 HRP:polymer and in the presence of NADPH. Data obtained are shown in FIG. 14. A linear dependence of the current density on NADPH concentration was observed in the 1–200 $\mu M$ NADPH range with a sensitivity again of $1Acm^{-2}M^{-1}$.

Equilibration times for steady state measurements depended upon the concentration of the mediator, i.e., a high mediator concentration resulted in acceleration of $H_2O_2$ production. Typically, a steady state current for injection of NADH was within 5% of its final value after five to seven minutes equilibration at 3.3 $\mu M$ 5-methylphenazonium methyl sulfate (PMS+) concentration.

As expected from reaction 3 discussed above, electroreduction currents were observed only in aerated or oxygenated solutions. The current did not increase when $O_2$ rather than air was bubbled through the solution, nor did the current decrease when the $O_2$ stream was replaced by air. When the solutions were purged of oxygen by bubbling of $N_2$, the current reversed, i.e., small electrooxidation current was observed in the PMSH (PMS+ and NADH) containing solution. Electrooxidation of PMSH proceeded on glassy carbon electrodes whether or not these were modified with HRP containing redox networks. However, even minimal aeration of the PMSH solution reversed the current. Such reversal was seen only on electrodes which contained HRP in the redox polymer network.

EXAMPLE 4

Preparation of Bi-layer $H_2O_2$ Sensing Electrodes

Polished rotating disk electrodes were prepared of vitreous carbon rods as described for Example 1.

A solution of 20mg/ml horseradish peroxidase (HRP) Type VI solution was prepared in 0.1 M $NaHCO_3$. A volume of 100 μl of this solution was reacted with 50 μl of $NaIO_4$ (12mg/ml) and incubated for two hours in the dark at room temperature. A volume of 10 μl of this oxidized HRP was added to a volume of 50 μl of Polymer I (PVP-Os-$NH_2$) (10mg/ml) and 60 μl of polyethylene glycol diglycidylether-400 (PEGDE). The polished electrode was coated with 3 μl of this mixture and cured for 48 hours in a vacuum desiccator.

D-amino acid oxidase (AAOX) bi-layer electrodes were prepared by placing a 10 μl aliquot of a solution containing 2.9mg/ml AAOX and 0.77% glutaraldehyde onto the cured HRP electrode and allowing this layer to incubate for at least two hours. Glucose oxidase (GOX) electrodes were prepared by reacting 100 μl GOX (20mg/ml), 10mM HEPES, pH8 with 50 μl $NaIO_4$ (12mg/ml) and incubating this mixture in the dark at room temperature for two hours. After incubation, 2 μl of the oxidized GOX was spread onto the prepared HRP electrode surface and allowed to incubate for at least two hours.

EXAMPLE 5

Use of Bi-layer Peroxidase-Glucose Oxidase Electrodes

A series of glucose electrodes were prepared as described in Example 4 using varying amounts of GOX ranging from 0.26 μg to 131 μg. These electrodes were applied to the assay of glucose in a three-electrode cell containing 25ml phosphate buffer solution (0.1M, pH 7.4). The working electrode was glassy carbon and a saturated calomel electrode (SCE) was used as the reference. A platinum wire was used as the auxiliary electrode. All of the measurements were performed in an open cell under air and at room temperature. All constant potential experiments were performed with a rotating disk electrode at 1000 rpm. The working electrode was typically poised at 0.0V (SCE) and the resulting current was measured.

Figure 15:
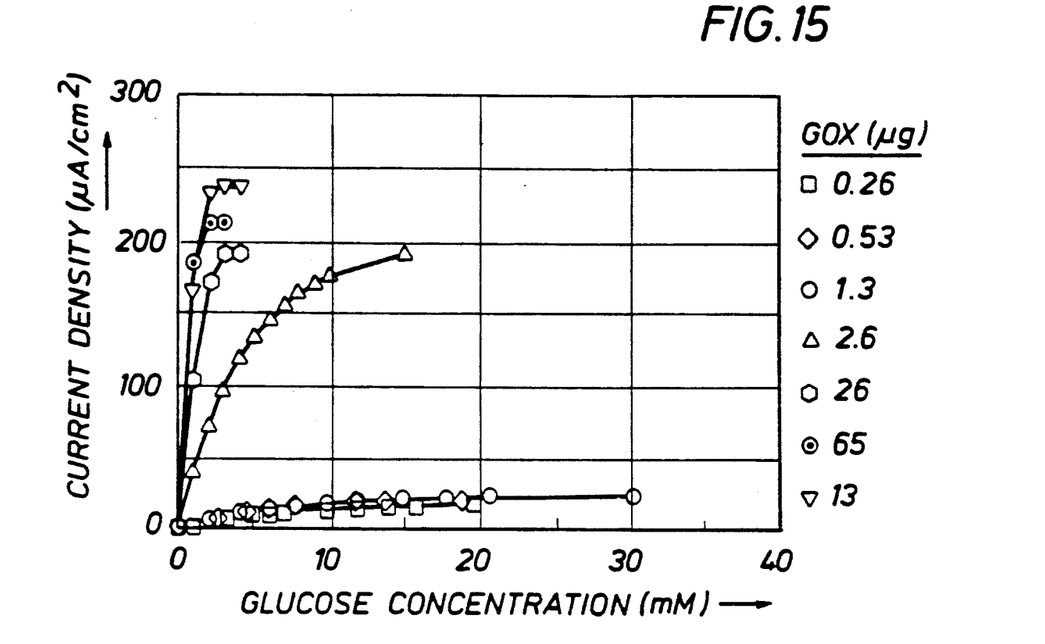
FIG. 15 is a graphical depiction of current density generated by an HRP-glucose oxidase (GOX) bilayer electrode in the presence of glucose, where the electrode contains 0.26–131 µg/GOX.
Figure 16:
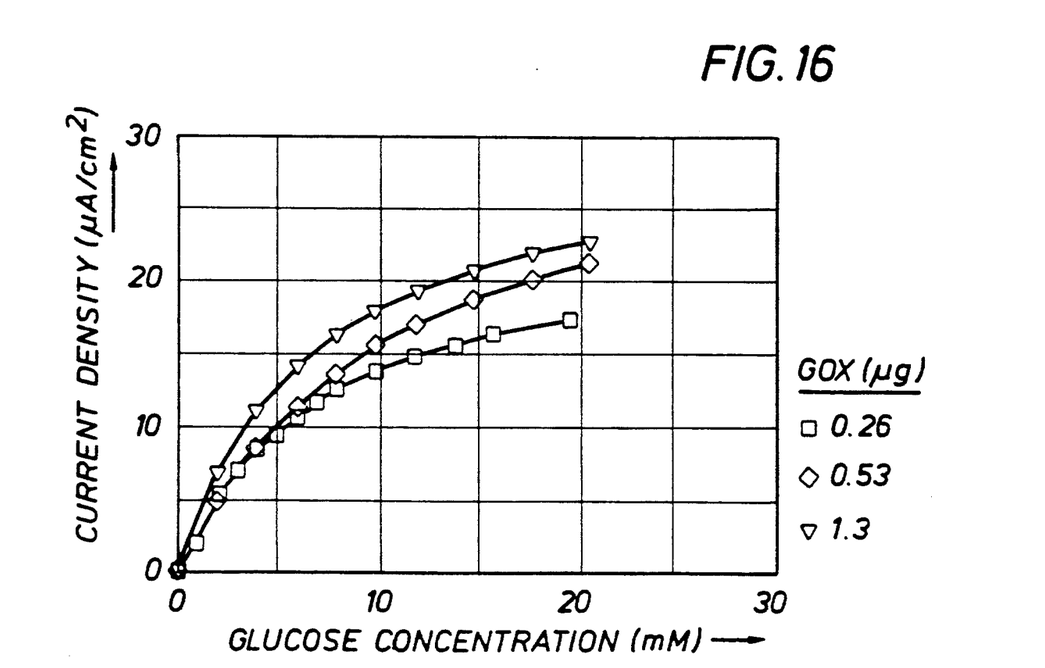
FIG. 16 is a graphical depiction of current density generated by an HRP-GOX bilayer electrode in the presence of glucose, where the electrode contains 0.26–1.3 µg/GOX.

Measurement of glucose in a test solution with the bi-layer peroxidase-glucose electrodes prepared with varying amounts of GOX was performed as described above. As a general trend, the magnitude of the response increased with increasing amounts of glucose oxidase, as shown in FIG. 15. The current response of electrodes prepared with 26 μg to 131 μg of glucose oxidase saturated at approximately 2mM glucose. This low dynamic range may be ascribed to oxygen depletion at the electrode surface. The electrodes prepared with 0.26 μg to 1.3 μg glucose oxidase all exhibited a linear response up to approximately 10 mM glucose as is better shown in FIG. 16.

A large decrease in catalytic current was observed when the amount of glucose oxidase was changed from 26 μg to 2.6 μg.

Figure 17:
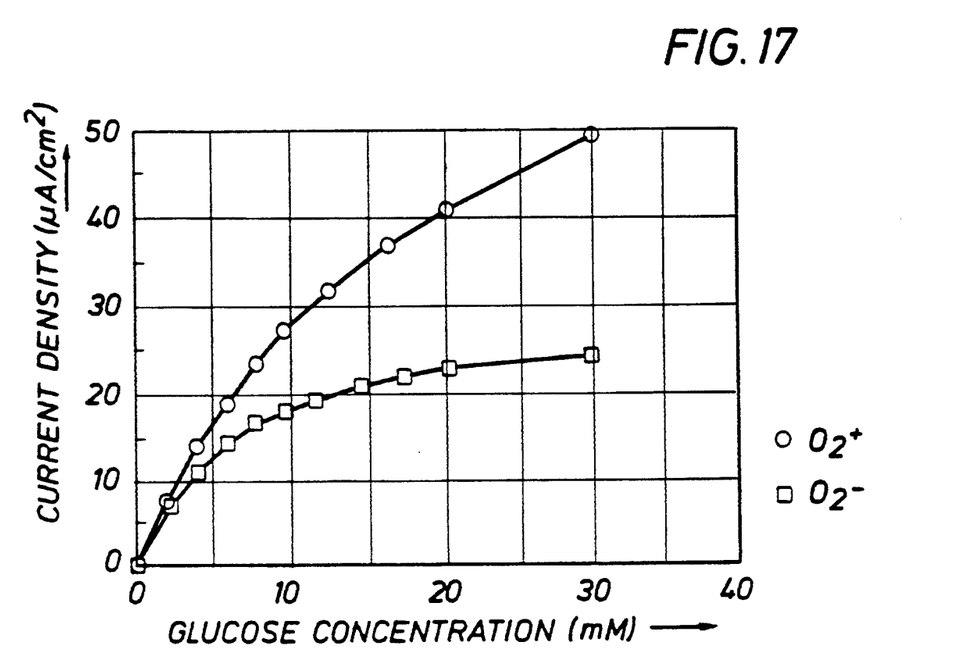
FIG. 17 is a graphical depiction of current density generated by an HRP-GOX bilayer electrode in the presence of glucose under oxygen saturation (open circles) and under partial depletion of oxygen (closed circles).

The experiments described above were repeated using a bi-layer peroxidase-glucose electrode containing 1.3 μg GOX in the presence and/or absence of oxygen being bubbled through the test solution. As shown in FIG. 17, the difference in catalytic current was small at glucose concentrations of less than 5mM when the solution was saturated with oxygen. However, there was a substantial difference seen in catalytic current at greater than 5mM glucose when the solution was oxygen-saturated.

Preliminary results on the stability of peroxidase-GOX electrodes demonstrated half lives of greater than 40 hours for continuous use at room temperature.

EXAMPLE 6

Use of Bi-layer Electrodes to Detect D-Amino Acids

Figure 18:
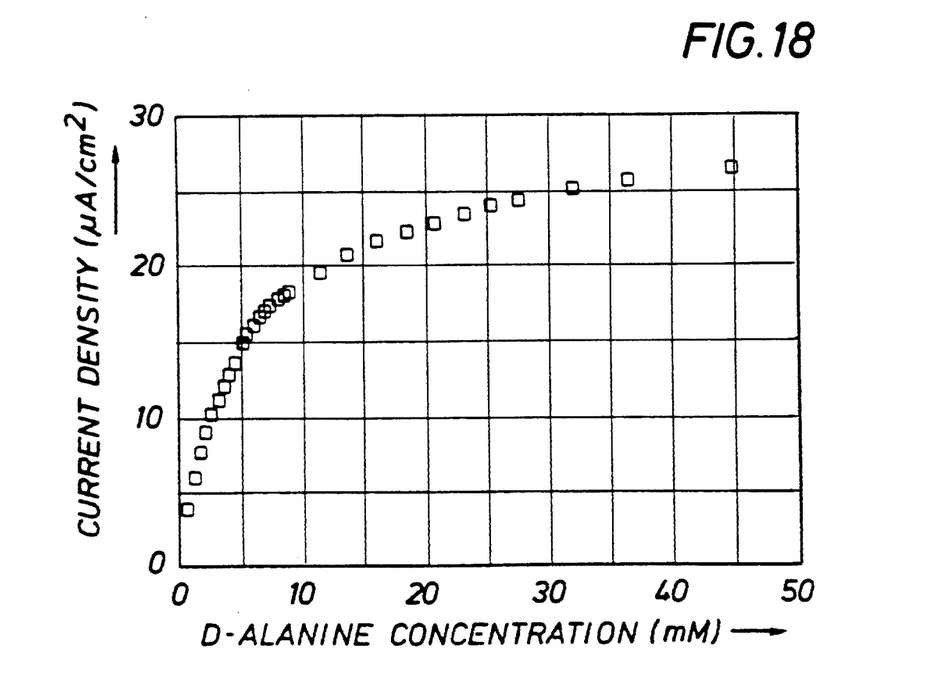
FIG. 18 is a graphical depiction of current density generated by a peroxidase-D-amino acid oxidase (AAOX) bilayer electrode in the presence of D-alanine.
Figure 19:
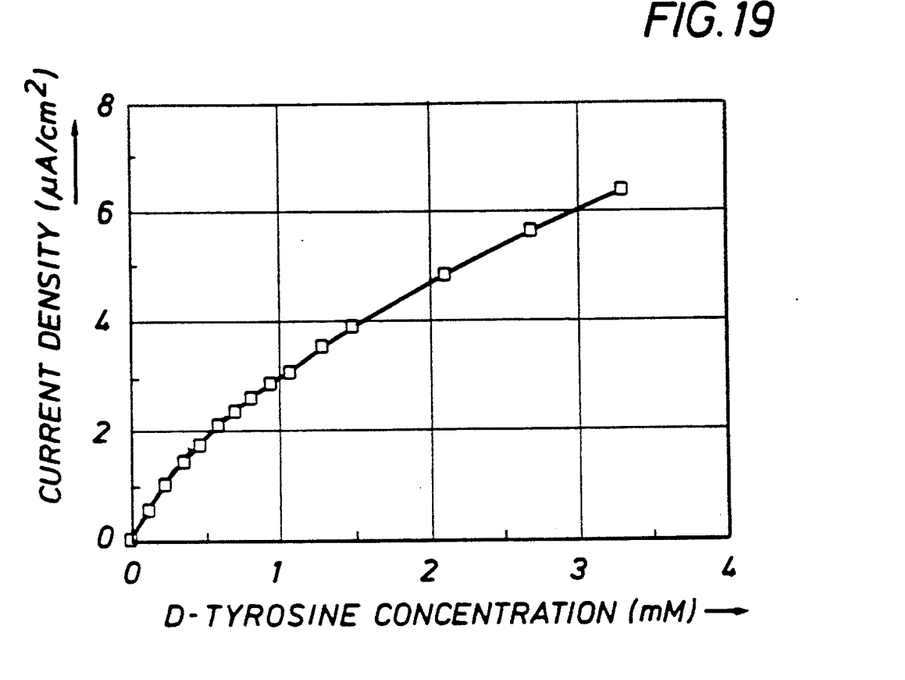
FIG. 19 is a graphical depiction of current density generated by a peroxidase-AAOX bilayer electrode in the presence of D-tyrosine.

The bi-layer peroxidase-D-amino acid electrodes prepared in Example 4 were tested in the assay of D-alanine, D-tyrosine, and D-cysteine. As shown in FIGS. 8 and 19, the steady state current response at 0.0V (SCE) exhibited a linear dynamic range of 0–2mM for D-alanine and 0–1mM for D-tyrosine. Response to D-cysteine was also observed.

Preliminary results with bi-layer peroxidase-AAOX electrodes have demonstrated half-lives, i.e., current decreased to half the initial current, of approximately 30 hours when used at room temperature and 16 hours at 37° C. for continuous operation of these electrodes.

EXAMPLE 7

Electrically Isolated Second Enzyme Containing Electrode

An electrode containing choline oxidase and horseradish peroxidase in a single layer was prepared as follows. Glassy carbon electrodes, 3 mm in diameter, were polished using diamond paste. A solution of polyaldehyde (i.e., $NaIO_4$-oxidized) horseradish peroxidase (HRP) was prepared by adding in a 1:2 ratio a 12 mg/ml solution of $NaIO_4$ to a 20 mg/ml solution of HRP (Type IV) in 0.1 M $NaHCO_3$. This solution was allowed to incubate in the dark for 2 hours. It was then mixed with a 10 mg/ml of Polymer I solution in a ratio of 1:5 HRP:Polymer I. A volume of 1 μl of this solution was then applied to the polished electrode surface along with 1 μl of 23 mg/ml choline oxidase solution and 1 μl of 1 mg/ml PEGDE 400 as a crosslinking agent. The solution was thoroughly mixed on the electrode surface and allowed to dry for at least 48 hours.

Figure 20:
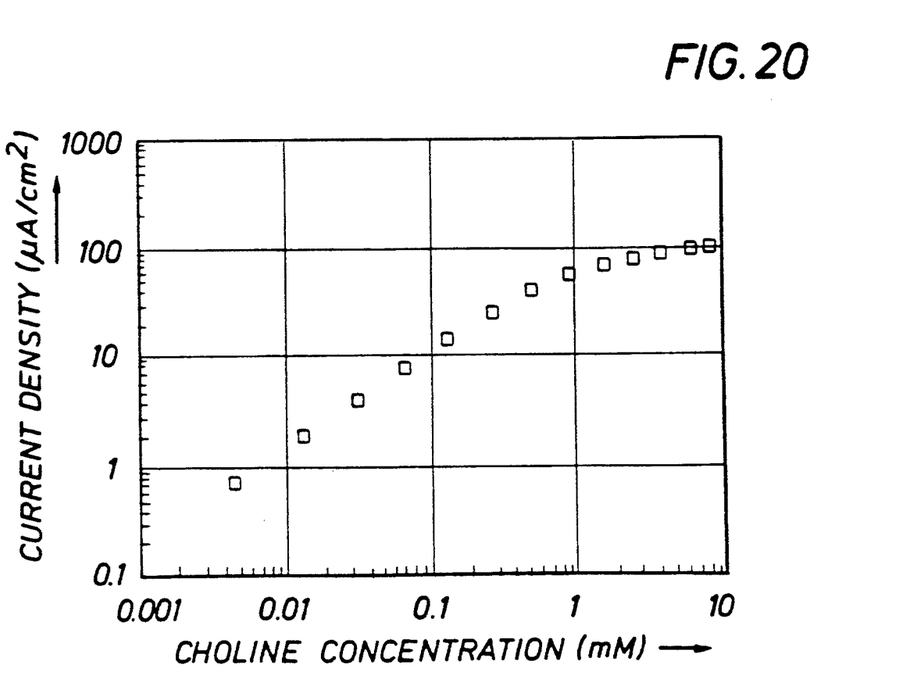
FIG. 20 is a graphical depiction of current density generated by a peroxidase-choline oxidase electrode in the presence of choline, where peroxidase and choline oxidase are present in a single electrode layer.

The resulting choline oxidase — peroxidase electrode was tested for its steady state current response at 0.0V (SCE) to increasing concentrations of choline substrate. The current increase at increasing choline concentrations is shown in FIG. 20.

We claim:

1. An electrode for the detection of hydrogen peroxide comprising:
    an electrode having a testing surface; and
    a transducing film substantially covering the testing surface of the electrode, the film comprising a cross-linked redox polymer network, the network comprising a redox compound having multiple redox centers and a peroxidase having redox centers wherein the redox centers of the peroxidase are electrically connected, in the absence of diffusional electron shuttles, to the electrode.

2. The electrode of claim 1, wherein the peroxidase is chemically bonded to the redox polymer network.

3. The electrode of claim 2, wherein the peroxidase is covalently bonded to the redox polymer network.

4. The electrode of claim 1, wherein the peroxidase is horseradish peroxidase.

5. The electrode of claim 1, wherein the peroxidase is fungal peroxidase of *Arthoromyces ramosus*.

6. The electrode of claim 1, wherein said peroxidase is a heme-containing molecule.

7. The electrode of claim 1, wherein the redox centers of the redox compound contain osmium.

8. The electrode of claim 7, wherein the redox compound is poly(vinyl pyridine) complexed with osmium bis(2,2'-bipyridine).

9. The electrode of claim 7, wherein the redox compound is poly (N-vinyl imidazole) complexed with osmium bis(2,2'-bipyridine).

10. The electrode of claim 1, further comprising an enzyme fixed to the network, which enzyme catalyzes a substrate-enzyme reaction generating $H_2O_2$, NADPH, or NADP, and wherein the enzyme is isolated from the peroxidase.

11. The electrode of claim 10, wherein the enzyme is physically isolated from the peroxidase.

12. The electrode of claim 11, wherein the enzyme is electrically isolated from the peroxidase.

13. A method for analyzing the presence of hydrogen peroxide in a test sample comprising the steps of:
contacting a test sample with an electrode having a test surface substantially covered with a transducing film comprising a cross-linked redox polymer network having multiple redox centers and peroxidase immobilized in the network;
generating electrons at the electrode;
transferring electrons from the electrode through the cross-linked polymer network to the peroxidase;
electroreducing hydrogen peroxide at the peroxidase;
generating an electrical current by electroreduction of hydrogen peroxide within the cross-linked redox polymer network; and
measuring the generated current.

14. The method of claim 13 wherein the peroxidase is covalently bound to the redox polymer network.

15. The method of claim 13, wherein the $H_2O_2$ present in the test sample is generated by a substrate-enzyme reaction such that the generated current is directly related to the amount of the substrate in the test sample.

16. A method for analyzing the presence of NADPH or NADH in a test sample comprising the steps of:
reacting NADPH or NADH with dissolved molecular oxygen in the presence of a quinoid in the test sample;
contacting the reacted test solution with an electrode having a testing surface substantially covered with a transducing film comprising a cross-linked redox polymer network having multiple redox centers and peroxidase immobilized in the network;
generating electrons at the electrode;
transferring electrons from the electrode through the cross-linked polymer network to the peroxidase;
electroreducing hydrogen peroxide at the immobilized peroxidase;
generating an electrical current by the transfer of electrons and electroreduction of hydrogen peroxide; and
quantifying the generated current.

17. The method of claim 16, wherein said NADPH or NADP present in the test sample is generated by substrateenzyme reaction such that the generated current is directly related to the amount of the substrate in the test sample.

* * * * *